US012208101B2

(12) United States Patent
Goncalves et al.

(10) Patent No.: US 12,208,101 B2
(45) Date of Patent: *Jan. 28, 2025

(54) TABLET FORMULATION OF 2-FLUORO-N-METHYL-4-[7-(QUINOLIN-6-YLMETHYL) IMIDAZO[1,2-B][1,2,4]TRIAZIN-2-YL]BENZ-AMIDE

(71) Applicant: Novartis AG, Basel (CH)

(72) Inventors: Elisabete Goncalves, Basel (CH); Christin Tauchmann, Bad Säckingen (DE); Sudha Vippagunta, Morris Plains, NJ (US); Shau-Fong Yen, Basel (CH); Zhixin Zong, Franklin Park, NJ (US)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/644,473

(22) Filed: Dec. 15, 2021

(65) Prior Publication Data

US 2022/0249498 A1    Aug. 11, 2022

Related U.S. Application Data

(60) Continuation of application No. 16/789,655, filed on Feb. 13, 2020, now abandoned, which is a continuation of application No. 16/134,162, filed on Sep. 18, 2018, now Pat. No. 10,596,178, which is a division of application No. 15/328,661, filed as application No. PCT/IB2015/055561 on Jul. 22, 2015, now Pat. No. 10,085,993.

(60) Provisional application No. 62/028,865, filed on Jul. 25, 2014.

(51) Int. Cl.
| A61K 31/53 | (2006.01) |
| A61J 3/06 | (2006.01) |
| A61K 9/20 | (2006.01) |
| A61K 31/517 | (2006.01) |
| A61K 31/5377 | (2006.01) |
| C07D 487/04 | (2006.01) |

(52) U.S. Cl.
CPC ............ *A61K 31/53* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2095* (2013.01); *A61K 31/517* (2013.01); *A61K 31/5377* (2013.01); *C07D 487/04* (2013.01); *A61J 3/06* (2013.01)

(58) Field of Classification Search
CPC .... A61K 31/53; A61K 9/2009; A61K 9/2013; A61K 9/2018; A61K 9/2027; A61K 9/2054; A61K 9/2095; A61K 31/517; A61K 31/5377; A61K 31/4985; A61K 2300/00; C07D 487/04; A61J 3/06; A61J 3/10; A61P 35/00; A61P 35/02

See application file for complete search history.

(56) References Cited

U.S. PATENT DOCUMENTS

| 7,676,765 | B2 | 3/2010 | Golibrodski et al. |
| 7,767,675 | B2 | 8/2010 | Zhuo et al. |
| 8,367,685 | B2 | 2/2013 | Adesuyi et al. |
| 8,420,645 | B2 | 4/2013 | Weng et al. |
| 8,461,330 | B2 | 6/2013 | Zhuo et al. |
| 8,518,446 | B2 | 8/2013 | Ashraf et al. |
| 10,085,993 | B2 | 10/2018 | Goncalves et al. |
| 10,596,178 | B2 * | 3/2020 | Goncalves ........... A61K 9/2095 |
| 2008/0167287 | A1 | 7/2008 | Zhuo et al. |
| 2008/0233188 | A1 | 9/2008 | Adesuyi et al. |
| 2009/0291956 | A1 | 11/2009 | Weng et al. |
| 2010/0204292 | A1 | 8/2010 | Aurora et al. |
| 2011/0111018 | A1 | 5/2011 | Ashraf et al. |
| 2013/0045245 | A1 | 2/2013 | Patel et al. |
| 2017/0231997 | A1 | 8/2017 | Goncalves et al. |
| 2019/0015418 | A1 | 1/2019 | Goncalves et al. |
| 2022/0249498 | A1 | 8/2022 | Goncalves et al. |

FOREIGN PATENT DOCUMENTS

| TW | I323661 B | 4/2010 |
| TW | I429432 B | 3/2014 |
| WO | WO 2004/110431 A1 | 12/2004 |
| WO | WO 2007/014124 A2 | 2/2007 |
| WO | WO 2007/031933 A2 | 3/2007 |
| WO | WO 2008/043167 A1 | 4/2008 |
| WO | WO 2008/064157 A1 | 5/2008 |
| WO | WO 2009/143211 A2 | 11/2009 |
| WO | WO 2011/055303 A1 | 5/2011 |
| WO | WO 2012/006298 A2 | 1/2012 |
| WO | WO 2014/028566 A1 | 2/2014 |

OTHER PUBLICATIONS

Golub, T. R., "Molecular classification of cancer: class discovery and class prediction by gene expression monitoring." Science (1999) 286: 531-537.*
Sawyers, C., "Targeted cancer therapy." Nature (2004)432: 294-297.*
Christensen, J. G., "A selective small molecule inhibitor of c-Met kinase inhibits c-Met-dependent phenotypes in vitro and exhibits cytoreductive antitumor activity in vivo." Cancer research (2003) 63: 7345-7355.*
Liu, X., "A Novel Kinase Inhibitor, INCB28060, Blocks c-MET—Dependent Signaling, Neoplastic Activities, and Cross-Talk with EGFR and HER-3INCB28060, a c-MET Kinase Selective Inhibitor." Clinical cancer research (2011)17: 7127-7138.*
U.S. Appl. No. 15/328,661 / 2017-0231997 A1 / U.S. Pat. No. 10,085,993, filed Jan. 24, 2017 / Aug. 17, 2017 / Oct. 2, 2018, Elisabete Goncalves.

(Continued)

*Primary Examiner* — John M Mauro
(74) *Attorney, Agent, or Firm* — Lathrop GPM LLP; Brian C. Trinque; Nicole Sassu

(57) ABSTRACT

The present invention is related to tablets comprising of 2-fluoro-N-methyl-4-[7-(quinolin-6-ylmethyl)imidazo[1,2-b][1,2,4]triazin-2-yl]benzamide, processes for the production thereof, and uses in the treatment of certain cancers.

9 Claims, 1 Drawing Sheet

(56) References Cited

OTHER PUBLICATIONS

U.S. Appl. No. 16/134,162 / 2019-0015418 A1 / U.S. Pat. No. 10,596,178, filed Sep. 18, 2018 / Jan. 17, 2019 / Mar. 24, 2020, Elisabete Goncalves.
U.S. Appl. No. 16/789,655 / 2021-0113569 A1, filed Feb. 13, 2020 / Apr. 22, 2021, Elisabete Goncalves.
Ansel et al., Pharmaceutical Dosage Forms and Drug Delivery Systems, Seventh Edition pp. 209-211 (1999).
Applicant's letter of Sep. 11, 2017 to the examiner during prosecution.
Aulton, Aulton's Pharmaceutics, The Design and Manufacture of Medicines, Third Edition, Chapter 22 "Assessment of biopharmaceutical properties", pp. 304-323 (2007).
Aulton, Pharmaceutics, The Science of Dosage Form Design, Second Edition, Chapter 27 "Tablets and compaction", pp. 398-410 (2006).
Clinical Trial NCT01610336, Jun. 4, 2012, available at https://clinicaltrials.gov/ct2/show/NCT01610336.
Clinical Trial NCT01737827, Nov. 30, 2012, available at https://clinicaltrials.gov/ct2/show/NCT01737827.
Dissolution testing protocol, 5 pages.
Egoshina et al., "Modern excipients in tablet production", *Advances in Modern Natural Science* 10:30-33 (2009).
Florence et al., Modern Pharmaceutics, Fifth Edition, Chapter 13 "Table Dosage Forms", pp. 481-497 (2009).
Gennaro et al., Remington's Pharmaceutical Sciences 18, Chapter 89 "Oral Solid Dosage Forms", pp. 1633-1658 (1990).
Gopinath et al., "A brief review on disintegrants", *Journal of Chemical and Pharmaceutical Sciences* 5(3):105-112, Jul.-Sep. 2012.
Japanese Pharmaceutical Excipients Directory, Yakuji Nippo, Limited, First Edition, pp. 93, 97, Jul. 25, 2007.
Lachman et al., The Theory and Practice of Industrial Pharmacy, Third Edition, pp. 321, 325-328 (1987).
Rahman et al., "Effect of mode of addition of disintegrants on dissolution of model drug from wet granulation tablets", *International Journal of Pharma Sciences and Research* 2(2):84-92 (2011).
Rowe et al., Handbook of Pharmaceutical Excipients, Sixth Edition, pp. 129-133, 208-210, 404-407, 424-428, 581-585, 728-730 (2009).
Swarbrick, Encyclopedia of Pharmaceutical Technology, Third Edition, vol. 1, "Tablet Formulation", pp. 3641-3672 (2007).
Wu et al., "Safety and efficacy of INC280 in combination with gefitinib (gef) in patients with EGFR-mutated (mut), MET-positive Nsclc: A single-arm phase lb/ll study", 2014 ASCO Annual Meeting I, Abstract 8017.
Granero et al., "Dissolution and Solubility Behavior of Fenofibrate in Sodium Lauryl Sulfate Solutions", *Drug Development and Industrial Pharmacy* 31(9):917-922 (2005).
Wang et al., Western Pharmaceutical Preparation Guide, Beijing: Military Medical Science Press, pp. 169-182 (2013).

\* cited by examiner

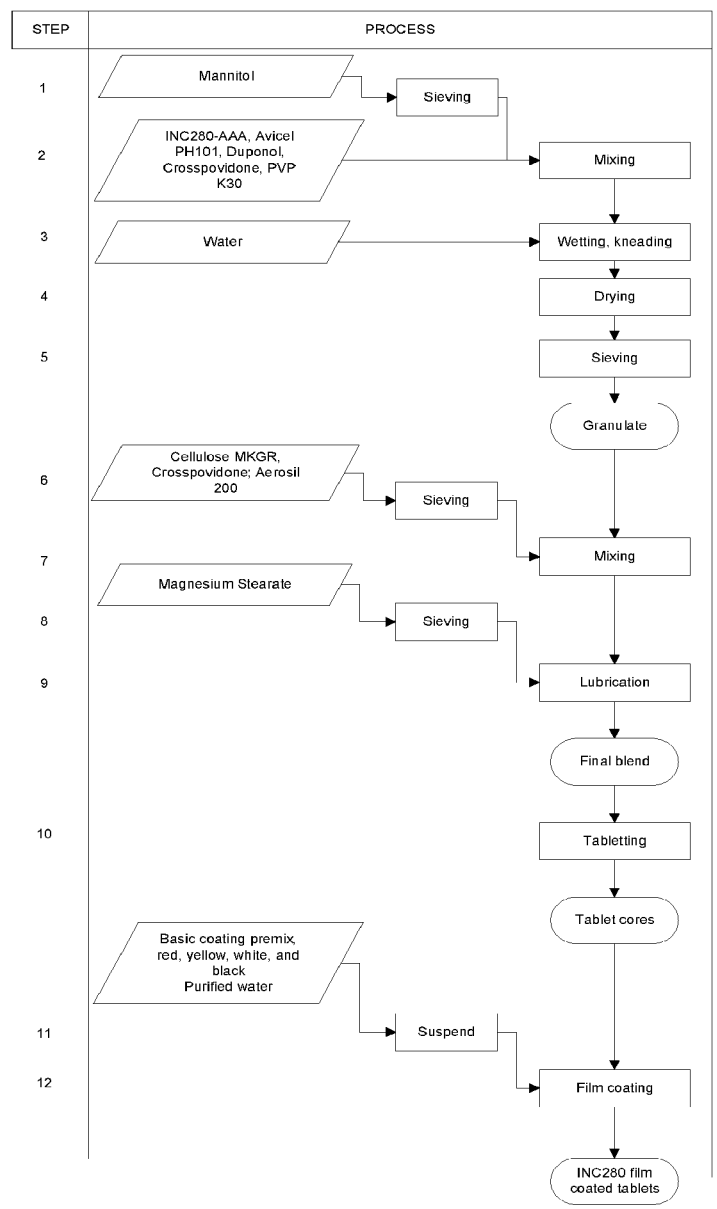

TABLET FORMULATION OF 2-FLUORO-N-METHYL-4-[7-(QUINOLIN-6-YLMETHYL)IMIDAZO[1,2-B][1,2,4]TRIAZIN-2-YL]BENZAMIDE

BACKGROUND

Protein kinases (PKs) are a group of enzymes that regulate diverse, important biological processes including cell growth, survival and differentiation, organ formation and morphogenesis, neovascularization, tissue repair and regeneration, among others. A subset of protein kinases (also referred to as oncogenic protein kinases), when dysregulated, can cause tumor formation and growth, and further contribute to tumor maintenance and progression (Blume-Jensen P. et al., Nature 2001, 411(6835):355-365). Thus far, oncogenic protein kinases represent one of the largest and most attractive groups of protein targets for cancer intervention and drug development. c-Met, a proto-oncogene, is a member of a distinct subfamily of heterodimeric receptor tyrosine kinases which include Met, Ron, and Sea (Birchmeier, C. et al., Nat. Rev. Mol. Cell Biol. 2003, 4(12):915-925; Christensen, J. G. et al., Cancer Lett. 2005, 225(1):1-26). The biological functions of c-Met (or c-Met signaling pathway) in normal tissues and human malignancies such as cancer have been well documented (Christensen, J. G. et al., Cancer Lett. 2005, 225(1):1-26; Corso, S. et al., Trends in Mol. Med. 2005, 11(6):284-292).

Dysregulated c-Met pathway plays important and sometimes causative (in the case of genetic alterations) roles in tumor formation, growth, maintenance and progression (Birchmeier, C. et al., Nat. Rev. Mol. Cell. Biol. 2003, 4(12):915-925; Boccaccio, C. et al., Nat. Rev. Cancer 2006, 6(8):637-645; Christensen, J. G. et al., Cancer Lett. 2005, 225(1):1-26). HGF (hepatocytic growth factor, a high affinity ligand for c-Met) and/or c-Met are overexpressed in significant portions of most human cancers, and are often associated with poor clinical outcomes such as more aggressive disease, disease progression, tumor metastasis and shortened patient survival. Further, patients with high levels of HGF/c-Met proteins are more resistance to chemotherapy and radiotherapy. The various cancers in which c-Met is implicated include, but are not limited to: carcinomas (e.g., bladder, breast, cervical, cholangiocarcinoma, colorectal, esophageal, gastric, head and neck, kidney, liver, lung, nasopharygeal, ovarian, pancreas, prostate, thyroid); musculoskeletal sarcomas (e.g., osteosarcaoma, synovial sarcoma, rhabdomyosarcoma); soft tissue sarcomas (e.g., MFH/fibrosarcoma, leiomyosarcoma, Kaposi's sarcoma); hematopoietic malignancies (e.g., multiple myeloma, lymphomas, adult T cell leukemia, acute myelogenous leukemia, chronic myeloid leukemia); and other neoplasms (e.g., glioblastomas, astrocytomas, melanoma, mesothelioma and Wilm's tumor (www.vai.org/met/; Christensen, J. G. et al., Cancer Lett. 2005, 225(1):1-26).

Inhibitors of c-Met and other kinases are reported in, e.g., U.S. Pat. No. 8,461,330, and include the compound 2-fluoro-N-methyl-4-[7-(quinolin-6-ylmethyl)imidazo[1,2-b][1,2,4]triazin-2-yl]benzamide (Compound I) having the structure indicated below.

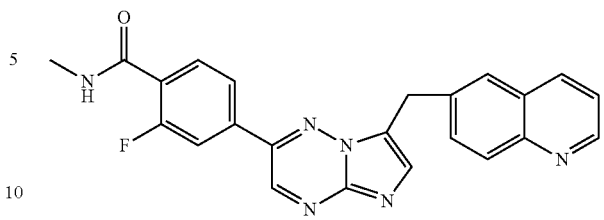

New or improved formulations of existing agents which inhibit kinases such as c-Met are continually needed for developing more effective pharmaceuticals to treat cancer and other diseases. Specifically, there is a need for pharmaceutical formulations comprising 2-fluoro-N-methyl-4-[7-(quinolin-6-ylmethyl)imidazo[1,2-b][1,2,4]triazin-2-yl]benzamide with increased dosage amounts, enhanced bioavailability, and improved dissolution at higher pHs (pH 4.5-6.8). These formulations, and methods described herein are directed toward these needs and other ends.

SUMMARY

Provided herein are pharmaceutical compositions comprising 2-fluoro-N-methyl-4-[7-(quinolin-6-ylmethyl)imidazo[1,2-b][1,2,4]triazin-2-yl]benzamide, or a pharmaceutically acceptable salt thereof and methods of use thereof.

In one aspect, provided herein is a tablet comprising 2-fluoro-N-methyl-4-[7-(quinolin-6-ylmethyl)imidazo[1,2-b][1,2,4]triazin-2-yl]benzamide, or a pharmaceutically acceptable salt thereof.

In an embodiment, the tablet comprises, by weight, 10-30% 2-fluoro-N-methyl-4-[7-(quinolin-6-ylmethyl)imidazo[1,2-b][1,2,4]triazin-2-yl]benzamide, or a pharmaceutically acceptable salt thereof, 50-70% of one or more fillers, 3-20% of one or more disintegrants, 0.2-2% of one or more lubricants, and 0.2-2% of one or more glidants.

In another embodiment, the tablet comprises mannitol, microcrystalline cellulose, polyvinylpolypyrrolidone, polyvinylpyrrolidone, colloidal silicon dioxide, and magnesium stearate.

In yet another embodiment, the tablet comprises an amount of 2-fluoro-N-methyl-4-[7-(quinolin-6-ylmethyl)imidazo[1,2-b][1,2,4]triazin-2-yl]benzamide, or a pharmaceutically acceptably salt thereof, wherein the amount corresponds to 5 mg, 10 mg, 20 mg, 25 mg, 40 mg, 50 mg, 75 mg, 100 mg, 125 mg, 150 mg, 200 mg, 250 mg, or 500 mg of the free base form. In a preferred embodiment, the tablet comprises 50 mg of the free base form of 2-fluoro-N-methyl-4-[7-(quinolin-6-ylmethyl)imidazo[1,2-b][1,2,4]triazin-2-yl]benzamide. In another preferred embodiment, the tablet comprises 100 mg of the free base form of 2-fluoro-N-methyl-4-[7-(quinolin-6-ylmethyl)imidazo[1,2-b][1,2,4]triazin-2-yl]benzamide.

In an embodiment of the tablets provided herein, the 2-fluoro-N-methyl-4-[7-(quinolin-6-ylmethyl)imidazo[1,2-b][1,2,4]triazin-2-yl]benzamide is present as the dihydrochloride salt.

In another aspect, provided herein is a tablet comprising 2-fluoro-N-methyl-4-[7-(quinolin-6-ylmethyl)imidazo[1,2-b][1,2,4]triazin-2-yl]benzamide, or a pharmaceutically acceptable salt thereof, wherein the tablet comprises:
(a) an intra-granular phase; and
(b) an extragranular phase.

In an embodiment, the tablet comprises, by weight, 10-30% 2-fluoro-N-methyl-4-[7-(quinolin-6-ylmethyl)imidazo[1,2-b][1,2,4]triazin-2-yl]benzamide, or a pharmaceutically acceptable salt thereof, 50-70% of one or more fillers, 3-20% of one or more disintegrants, 0.2-2% of one or more lubricants, and 0.2-2% of one or more glidants.

In an embodiment, the intra-granular phase comprises 2-fluoro-N-methyl-4-[7-(quinolin-6-ylmethyl)imidazo[1,2-b][1,2,4]triazin-2-yl]benzamide or a pharmaceutically acceptable salt thereof, mannitol, microcrystalline cellulose, polyvinylpolypyrrolidone, and polyvinylpyrrolidone.

In an embodiment, the extra-granular phase comprises microcrystalline cellulose, colloidal silicon dioxide, polyvinylpolypyrrolidone, and magnesium stearate.

In an embodiment of the tablets provided herein, the 2-fluoro-N-methyl-4-[7-(quinolin-6-ylmethyl)imidazo[1,2-b][1,2,4]triazin-2-yl]benzamide is present as the dihydrochloride salt.

In another aspect, provided herein is a method of treating cancer in an individual in need thereof, comprising administering to the individual the tablet provided herein. In an embodiment, the cancer is a solid tumor. In another embodiment, the cancer is lung cancer, liver cancer, gastric cancer, a glioblastoma, breast cancer, gastric cancer, kidney cancer, or nasopharyngeal cancer. In preferred embodiments, the cancer is non-small cell lung cancer, hepatocellular carcinoma, or renal cell carcinoma.

In another aspect, provided herein is tablet comprising 2-fluoro-N-methyl-4-[7-(quinolin-6-ylmethyl)imidazo[1,2-b][1,2,4]triazin-2-yl]benzamide, or a pharmaceutically acceptable salt thereof, wherein the tablet comprises:
(a) an intragranular phase comprising, by weight:
   10-30% of 2-fluoro-N-methyl-4-[7-(quinolin-6-ylmethyl)imidazo[1,2-b][1,2,4]triazin-2-yl]benzamide dihydrochloric acid salt,
   10-30% of mannitol,
   10-30% of microcrystalline cellulose,
   0.1-1% of sodium dodecyl sulfate,
   1-10% of polyvinylpolypyrrolidone, and
   1-10% of polyvinylpyrrolidone; and
(b) an extragranular phase comprising, by weight:
   10-30% of microcrystalline cellulose,
   0.1-1% of colloidal silicon dioxide,
   1-10% of polyvinylpolypyrrolidone, and
   0.1-1% of magnesium stearate;
wherein the percentages given for the respective ingredients are relative to the total weight of the tablet.

In another aspect, provided herein is a tablet comprising 2-fluoro-N-methyl-4-[7-(quinolin-6-ylmethyl)imidazo[1,2-b][1,2,4]triazin-2-yl]benzamide, or a pharmaceutically acceptable salt thereof, wherein the tablet comprises:
(a) an intragranular phase comprising, by weight: about:
   23.54% of 2-fluoro-N-methyl-4-[7-(quinolin-6-ylmethyl)imidazo[1,2-b][1,2,4]triazin-2-yl]benzamide dihydrochloric acid salt,
   20% of mannitol,
   20.26% of microcrystalline cellulose,
   0.2% of sodium dodecyl sulfate,
   5% of polyvinylpolypyrrolidone, and
   4% of polyvinylpyrrolidone; and
(b) an extragranular phase comprising, by weight, about:
   20.75% of microcrystalline cellulose,
   0.5% of colloidal silicon dioxide,
   5% of polyvinylpolypyrrolidone, and
   0.75% of magnesium stearate;
wherein the percentages given for the respective ingredients are relative to the total weight of the tablet.

In another aspect, provided herein is a process for the production of a tablet comprising 2-fluoro-N-methyl-4-[7-(quinolin-6-ylmethyl)imidazo[1,2-b][1,2,4]triazin-2-yl]benzamide or a pharmaceutically acceptable salt thereof, wherein the process comprises:
(a) blending excipients together with 2-fluoro-N-methyl-4-[7-(quinolin-6-ylmethyl)imidazo[1,2-b][1,2,4]triazin-2-yl]benzamide;
(b) granulating the mixture formed in step (a) together with water;
(c) drying the granulate formed in step (b);
(d) passing the granulate of step (c) through a sieve to form the intra-granular phase;
(e) separately sieving suitable excipients as an extragranular phase;
(f) blending together the intragranular phase formed in step (d) with the extra-granular phase formed in step (e);
(g) adding a lubricant to the formulation to the mixture formed in step (f) and blending; and
(h) compressing the mixture formed in step (g) into tablets.

BRIEF DESCRIPTION OF THE DRAWINGS

FIG. 1 depicts a flow diagram of the manufacturing process used for the manufacture of tablets comprising 2-fluoro-N-methyl-4-[7-(quinolin-6-ylmethyl)imidazo[1,2-b][1,2,4]triazin-2-yl]benzamide.

DETAILED DESCRIPTION

Provided herein are pharmaceutical compositions comprising 2-fluoro-N-methyl-4-[7-(quinolin-6-ylmethyl)imidazo[1,2-b][1,2,4]triazin-2-yl]benzamide, or a pharmaceutically acceptable salt thereof and methods of use thereof specifically, provided herein are tablets comprising 2-fluoro-N-methyl-4-[7-(quinolin-6-ylmethyl)imidazo[1,2-b][1,2,4]triazin-2-yl]benzamide. The tablets of the invention provide several advantageous features including increased dosage amounts and enhanced bioavailability.

Certain terms used herein are described below. Compounds of the present invention are described using standard nomenclature. Unless defined otherwise, all technical and scientific terms used herein have the same meaning as is commonly understood by one of skill in the art to which this invention belongs.

Compound I: 2-fluoro-N-methyl-4-[7-(quinolin-6-ylmethyl)imidazo[1,2-b][1,2,4]triazin-2-yl]benzamide The synthesis and characterization of Compound I (2-fluoro-N-methyl-4-[7-(quinolin-6-ylmethyl)imidazo[1,2-b][1,2,4]triazin-2-yl]benzamide) is described in U.S. Pat. No. 8,461,330, which is hereby incorporated in its entirety.

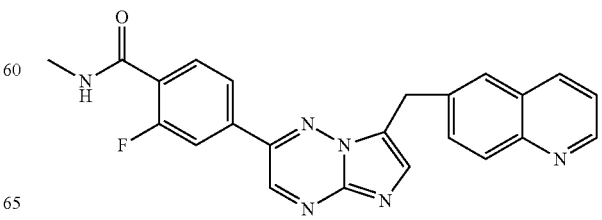

(I)

In an embodiment, Compound I is in the form of the dihydrochloric acid salt (e.g., Compound I·2HCl), a form described in U.S. Pat. No. 8,420,645, which is also hereby incorporated in its entirety. It is understood that the salt may be crystalline in form, or in the form of a hydrate or solvate. In a preferred embodiment, Compound I is in the form of the dihydrochloride monohydrate salt (also described in U.S. Pat. No. 8,420,645).

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, PA, 1985, which is incorporated herein by reference or S. M. Berge, et al., "Pharmaceutical Salts," J. Pharm. Sci., 1977; 66:1-19 both of which are incorporated herein by reference.

Tablets Comprising Compound I

The term "tablet" denotes an orally administrable, single-dose, solid dosage form that can be produced by compressing the drug substance (2-fluoro-N-methyl-4-[7-(quinolin-6-ylmethyl)imidazo[1,2-b][1,2,4]triazin-2-yl]benzamide or a pharmaceutically acceptable salt thereof, see e.g., U.S. Pat. No. 8,461,330, which is hereby incorporated in its entirety) with suitable excipients (e.g., fillers, disintegrants, lubricants, glidants, and/or surfactants) by conventional tableting processes. The term "film-coated tablet" refers to a tablet with a coating. The tablet can be produced using conventional granulation methods, for example, wet or dry granulation, with optional comminution of the granules with subsequent compression and optional coating. In an embodiment, the tablets of the instant invention comprise an intra- and extra-granular phase. The tablets can be optionally coated with various conventional coatings to form a film-coated tablet.

The active ingredient, Compound I (corresponding to the free base form), comprises, by weight, from about 10% to about 70%, including from about 10% to about 30% and about 23% to about 25%, based upon the total weight of the formulation.

As used herein, a % by weight of the formulation indicates a % by weight of the tablet, unless otherwise indicated.

As used herein, the term "about" refers to plus or minus 10% of the value.

In a preferred embodiment, the active ingredient, Compound I, will be in the form of the dihydrochlorid acid salt (see, e.g., U.S. Pat. No. 8,420,645).

The tablet of the invention comprises, by weight, from about 50% to about 70% of one or more fillers. Suitable fillers or "diluents" are known in the art, and include but are not limited to starch, dextrin, sucrose, sorbitol, sodium saccharin, acesulfame potassium, xylitol, aspartame, mannitol, starch, PVP (polyvinyl pyrrolidone), low molecular weight HPC (hydroxypropyl cellulose), microcrystalline cellulose (MCC), low molecular weight HPMC (hydroxypropylmethylcellulose), low molecular weight carboxymethyl cellulose, ethylcellulose, dicalcium phosphate, silicified microcrystalline cellulose, alginates, gelatin, polyethylene oxide, acacia, dextrin, sucrose, magnesium aluminum silicate, and polymethacrylates. Fillers also include agents selected from the group consisting of microcrystalline cellulose, starch, lactitol, lactose, a suitable inorganic calcium salt, sucrose, glucose, mannitol, silicic acid, and any combination thereof. The fillers as an intragranular component, comprise, by weight, from about 15% to about 65%, based upon total weight of the tablet formulation. In an embodiment, the intragranular filler comprises mannitol and microcrystalline cellulose (such as, e.g., Avicel PH 101). In other embodiments, the mannitol and microcrystalline cellulose are present in a ratio of about 1:1, 2:1, or 3:1 (mannitol to microcrystalline cellulose, by weight). In another embodiment, the mannitol and microcrystalline cellulose are present in a ratio of about 1:3 (mannitol to microcrystalline cellulose, by weight) when the tablet comprises higher levels of disintegrants. The fillers, as an extragranular component comprise, by weight, from about 15% to about 25%, based upon the total weight of the tablet formulation. In an embodiment, the extragranular filler is microcrystalline cellulose (such as, e.g., Cellulose MK GR).

The tablet of the invention comprises, by weight, about 3% to about 20%, of one or more disintigrants. In an embodiment, the tablet comprises about 10% to about 20% of one or more disintegrants. Suitable disintegrants are known in the art and include, but are not limited to, agar, calcium carbonate, potato or tapioca starch, alginic acid, certain silicates, sodium carbonate, crospovidone (cross-linked PVP, or polyvinylpolypyrrolidone, such as e.g., Polyvinylpolypyrrolidone XL), PVP or polyvinylpyrrolidone (e.g., Polyvinyl pyrrolidone K30 PH), sodium carboxymethyl starch (sodium starch glycolate), cross-linked sodium carboxymethyl cellulose (croscarmellose), pregelatinized starch (starch 1500), microcrystalline starch, water insoluble starch, sodium starch glycolate, potassium polacrilin, sodium alginate, calcium carboxymethyl cellulose, magnesium aluminum silicate (Veegum) and any combination thereof. In some embodiments, the disintegrant is polyvinylpolypyrrolidone or polyvinylpyrrolidone or a combination thereof. The disintegrant as an intragranular component, comprises, by weight, from about 5% to about 15%, including about 2% to 12%, based upon the total weight of the tablet formulation. The disintegrant as an extragranular component, comprises, by weight, from about 1% to about 8%, based upon total weight of the tablet formulation. In some embodiments, the disintegrant of the extragranular component is polyvinylpolypyrrolidone (e.g., Polyvinylpolypyrrolidone XL).

Glidants can also be used in the pharmaceutical formulation provided herein. In an embodiment, the tablet of the invention comprises, by weight, about 0.2% to about 2% of one or more glidants. Suitable glidants include, without limitation, colloidal silicon dioxide, talc, magnesium carbonate, calcium silicate, fumed silicon dioxide, and any combination thereof. In an embodiment, the glidant is an extragranular component of the formulation. In some embodiments, the glidant is colloidal silicon dioxide (e.g., hydrophilic fumed silica such as Aerosil 200). The amount of glidants used can be, by weight, about 0.2% to 2%, or about 0.2% to 1%, based on the total weight of the tablet formulation.

Lubricants can also be used in the pharmaceutical formulations provided herein. In an embodiment, the tablet of the invention comprises, by weight, about 0.2% to about 2% of one or more lubricants. Suitable lubricants include, for example, stearates, sodium stearyl fumarate, magnesium salts, and magnesium stearate. In an embodiment, the lubricant is used as an extragranular component of the formulation. In another embodiment, the lubricant is magnesium stearate. The amount of lubricant used can be, by weight, about 0.2% to 2%, or about 0.5% to 1.5%, based on the total weight of the tablet formulation.

Other excipients such as surfactants can be used in the instant formulations. In an embodiment, the tablet of the invention comprises, by weight, about 0 to about 10% of one or more surfactants. In an embodiment, the surfactant is used as an intragranular component of the formulation. In an embodiment, the pharmaceutical formulation comprises poloxamer (e.g., Poloxamer 188) or sodium dodecyl sulfate (e.g., Duponol C). The amount of surfactant used can be, by weight, about 0 to 10%, about 0.05% to 11 %, or about 0.1% to 0.5%, based on the total weight of the tablet formulation. In an embodiment, the formulation provided herein does not include a surfactant.

The tablets provided herein can be formulated in a unit dosage form, each dosage containing from about 5 to about 500 mg, more usually about 50 to about 200 mg, of the active ingredient. In some embodiments, the unit dosage form contains 5 mg, 10 mg, 20 mg, 25 mg, 40 mg, 50 mg, 75 mg, 100 mg, 125 mg, 150 mg, 200 mg, 250 mg, or 500 mg of Compound I. In some embodiments, the unit dosage form contains between 5 mg and 500 mg, inclusive, of Compound I. In other embodiments, the unit dosage form contains between 50 mg and 200 mg, inclusive, of Compound I or between 75 mg and 150 mg, inclusive, of Compound I. In preferred embodiments, the unit dosage form contains 50 mg or 100 mg of Compound I. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. In an embodiment, the unit dosage form will be equivalent to a therapeutically effective dose of the active ingredient (e.g., Compound I).

The tablets provided herein can be film-coated tablets, wherein a tablet further comprises a film coating. The film-coating can comprise one or more film-forming substances and can further comprise substances such as plasticizers, intestinal lubricants, or colorants. In an embodiment, the film coating comprises colorants or pigments.

In an embodiment, the tablet comprises, by weight, 10-30% 2-fluoro-N-methyl-4-[7-(quinolin-6-ylmethyl)imidazo[1,2-b][1,2,4]triazin-2-yl]benzamide, or a pharmaceutically acceptable salt thereof, 50-70% of one or more fillers, 3-20% of one or more disintegrants, 0.2-2% of one or more lubricants, and 0.2-2% of one or more glidants.

In another embodiment, the tablet further comprises 0.05-1% of one or more surfactants.

In another embodiment, the tablet comprises mannitol, microcrystalline cellulose, polyvinylpolypyrrolidone, polyvinylpyrrolidone, colloidal silicon dioxide, and magnesium stearate.

In another embodiment, the tablet further comprises sodium dodecyl sulfate.

In yet another embodiment, the tablet comprises an amount of 2-fluoro-N-methyl-4-[7-(quinolin-6-ylmethyl)imidazo[1,2-b][1,2,4]triazin-2-yl]benzamide, or a pharmaceutically acceptably salt thereof, wherein the amount corresponds to 5 mg, 10 mg, 20 mg, 25 mg, 40 mg, 50 mg, 75 mg, 100 mg, 125 mg, 150 mg, 200 mg, 250 mg, or 500 mg of the free base form. In a preferred embodiment, the tablet comprises 50 mg of the free base form of 2-fluoro-N-methyl-4-[7-(quinolin-6-ylmethyl)imidazo[1,2-b][1,2,4]triazin-2-yl]benzamide. In another preferred embodiment, the tablet comprises 100 mg of the free base form of 2-fluoro-N-methyl-4-[7-(quinolin-6-ylmethyl)imidazo[1,2-b][1,2,4]triazin-2-yl]benzamide.

In another aspect, provided herein is a tablet comprising 2-fluoro-N-methyl-4-[7-(quinolin-6-ylmethyl)imidazo[1,2-b][1,2,4]triazin-2-yl]benzamide, or a pharmaceutically acceptable salt thereof, wherein the tablet comprises:
(a) an intra-granular phase; and
(b) an extra-granular phase.

In an embodiment, the tablet comprises, by weight, 10-30% 2-fluoro-N-methyl-4-[7-(quinolin-6-ylmethyl)imidazo[1,2-b][1,2,4]triazin-2-yl]benzamide, or a pharmaceutically acceptable salt thereof, 50-70% of one or more fillers, 3-20% of one or more disintegrants, 0.2-2% of one or more lubricants, 0.2-2% of one or more glidants. In another embodiment, the tablet further comprises 0.05-1% of one or more surfactants.

In an embodiment, the intra-granular phase comprises 2-fluoro-N-methyl-4-[7-(quinolin-6-ylmethyl)imidazo[1,2-b][1,2,4]triazin-2-yl]benzamide or a pharmaceutically acceptable salt thereof, mannitol, microcrystalline cellulose, polyvinylpolypyrrolidone, and polyvinylpyrrolidone. In another embodiment, the intra-granular phase further comprises sodium dodecyl sulfate.

In a further embodiment, the intra-granular phase comprises, by weight of the tablet, 10-30% 2-fluoro-N-methyl-4-[7-(quinolin-6-ylmethyl)imidazo[1,2-b][1,2,4]triazin-2-yl]benzamide or a pharmaceutically acceptable salt thereof; 10-30% mannitol; 10-30% microcrystalline cellulose; and 0.1-10.0% each of polyvinylpolypyrrolidone and polyvinylpyrrolidone. In a further embodiment, the intra-granular phase further comprises 0.1-1% of sodium dodecyl sulfate.

In yet a further embodiment, the intra-granular phase comprises, by weight of the tablet, about 24% 2-fluoro-N-methyl-4-[7-(quinolin-6-ylmethyl)imidazo[1,2-b][1,2,4]triazin-2-yl]benzamide or a pharmaceutically acceptable salt thereof, about 20% mannitol; about 20% microcrystalline cellulose; about 5% polyvinylpolypyrrolidone; and about 4% polyvinylpyrrolidone. In a further embodiment, the intra-granular phase further comprises about 0.2% of sodium dodecyl sulfate.

In an embodiment, the extra-granular phase comprises microcrystalline cellulose, colloidal silicon dioxide, polyvinylpolypyrrolidone, and magnesium stearate.

In another embodiment, the extra-granular phase comprises, by weight of the tablet, 10-30% microcrystalline cellulose and 0.1-10.0% each of colloidal silicon dioxide, polyvinylpolypyrrolidone, and magnesium stearate.

In yet another embodiment, the extra-granular phase comprises, by weight of the tablet, about 21% microcrystalline cellulose; about 0.5% colloidal silicon dioxide; 5% polyvinylpolypyrrolidone; and about 0.75% magnesium stearate.

In an embodiment of the tablets provided herein, the 2-fluoro-N-methyl-4-[7-(quinolin-6-ylmethyl)imidazo[1,2-b][1,2,4]triazin-2-yl]benzamide is present as the dihydrochloride salt.

In another aspect, provided herein is a tablet comprising 2-fluoro-N-methyl-4-[7-(quinolin-6-ylmethyl)imidazo[1,2-b][1,2,4]triazin-2-yl]benzamide, or a pharmaceutically acceptable salt thereof, wherein the tablet comprises:
(a) an intragranular phase comprising, by weight:
10-30% of 2-fluoro-N-methyl-4-[7-(quinolin-6-ylmethyl)imidazo[1,2-b][1,2,4]triazin-2-yl]benzamide dihydrochloric acid salt,
10-30% of mannitol,
10-30% of microcrystalline cellulose,
0.1-1% of sodium dodecyl sulfate,
1-10% of polyvinylpolypyrrolidone, and
1-10% of polyvinylpyrrolidone; and
(b) an extragranular phase comprising, by weight:
10-30% of microcrystalline cellulose, 0.1-1% of colloidal silicon dioxide,
1-10% of polyvinylpolypyrrolidone, and
0.1-1% of magnesium stearate;
wherein the percentages given for the respective ingredients are relative to the total weight of the tablet.

In another aspect, provided herein is a tablet comprising 2-fluoro-N-methyl-4-[7-(quinolin-6-ylmethyl)imidazo[1,2-b][1,2,4]triazin-2-yl]benzamide, or a pharmaceutically acceptable salt thereof, wherein the tablet comprises:
(a) an intragranular phase comprising, by weight, about:
   24% of 2-fluoro-N-methyl-4-[7-(quinolin-6-ylmethyl)imidazo[1,2-b][1,2,4]triazin-2-yl]benzamide dihydrochloric acid salt,
   20% of mannitol,
   20% of microcrystalline cellulose,
   0.2% of sodium dodecyl sulfate,
   5% of polyvinylpolypyrrolidone, and
   4% of polyvinylpyrrolidone; and
(b) an extragranular phase comprising, by weight, about:
   21% of microcrystalline cellulose,
   0.5% of colloidal silicon dioxide,
   5% of polyvinylpolypyrrolidone, and
   0.75% of magnesium stearate;
wherein the percentages given for the respective ingredients are relative to the total weight of the tablet.

Methods of Treatment

The present invention further provides methods of treating diseases associated with a dysregulated kinase signaling pathway, including abnormal activity and/or overexpression of the protein kinase, in an individual (e.g., patient) by administering the tablet of the invention to the individual in need of such treatment. In some embodiments, the dysregulated kinase is of the Met family (e.g., c-Met, Ron, or Sea). In some embodiments, the dysregulated kinase is overexpressed in the diseased tissue of the patient. In some embodiments, the dysregulated kinase is abnormally active in the diseased tissue of the patient. Dysregulation of c-Met and the HGF/c-Met signaling pathway is meant to include activation of the enzyme through various mechanisms including, but not limited to, HGF-dependent autocrine and paracrine activation, c-met gene overexpression and amplification, point mutations, deletions, truncations, rearrangement, as well as abnormal c-Met receptor processing and defective negative regulatory mechanisms.

In some embodiments, the tablet of the invention is useful in treating diseases such as cancer, atherosclerosis, lung fibrosis, renal fibrosis and regeneration, liver disease, allergic disorder, inflammatory disease, autoimmune disorder, cerebrovascular disease, cardiovascular disease, or condition associated with organ transplantation. In further embodiments, the compounds of the invention can be useful in methods of inhibiting tumor growth or metastasis of a tumor in a patient.

Example cancers treatable by the methods herein include bladder cancer, breast cancer, cervical cancer, cholangiocarcinoma cancer, colorectal cancer, esophageal cancer, gastric cancer, head and neck cancer, cancer of the kidney, liver cancer, lung cancer, nasopharygeal cancer, ovarian cancer, pancreatic cancer, prostate cancer, thyroid cancer, osteosarcoma, synovial sarcoma, rhabdomyosarcoma, MFH/fibrosarcoma, leiomyosarcoma, Kaposi's sarcoma, multiple myeloma, lymphoma, adult T cell leukemia, acute myelogenous leukemia, chronic myeloid leukemia, glioblastoma, astrocytoma, melanoma, mesothelioma, or Wilm's tumor, and the like.

In an aspect, provided herein are methods for the treatment of cancer in an individual in need thereof, comprising administering to the individual the tablet of the invention.

In an embodiment, the cancer is a solid tumor. In another embodiment, the cancer is lung cancer, liver cancer, gastric cancer, a glioblastoma, breast cancer, gastric cancer, kidney cancer, or nasopharyngeal cancer. In preferred embodiments, the cancer is non-small cell lung cancer, hepatocellular carcinoma, or renal cell carcinoma.

In an embodiment of the methods provided herein, the treatment comprises the administration of an additional anticancer agent selected from the group consisting of erlotinib, gefitinib, and buparlisib.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Processes to Produce Tablets Comprising Compound I

Provided herein are processes for the production of a tablet comprising 2-fluoro-N-methyl-4-[7-(quinolin-6-ylmethyl)imidazo[1,2-b][1,2,4]triazin-2-yl]benzamide or a pharmaceutically acceptable salt thereof. These processes comprise compressing the drug substance with suitable excipients by conventional tableting processes and subsequently coating the core. The tablets can be produced using conventional granulation methods, for example, wet or dry granulation, with optional comminution of the granules with subsequent compression and coating. In an embodiment, the process comprises blending an intra- and extra-granular phase and compression of the mixture to form tablets. In an embodiment, the process comprises addition of a lubricant. The tablets can be optionally coated with various conventional coatings to form a film-coated tablet. An example of a suitable process to form tablets or film-coated tablets is described in Example 2, and illustrated in FIG. 1.

In an aspect, provided herein is a process for the production of a tablet comprising 2-fluoro-N-methyl-4-[7-(quinolin-6-ylmethyl)imidazo[1,2-b][1,2,4]triazin-2-yl]benzamide or a pharmaceutically acceptable salt thereof, wherein the process comprises:
(a) blending excipients together with 2-fluoro-N-methyl-4-[7-(quinolin-6-ylmethyl)imidazo[1,2-b][1,2,4]triazin-2-yl]benzamide or a pharmaceutically acceptable salt thereof to form an intragranular phase;
(b) blending suitable excipients as an extragranular;
(c) blending together the intragranular phase formed in step (a) with the extra-granular phase formed in step (b); and
(d) compressing the mixture formed in step (c) into tablets.

In an embodiment, the process further comprises the step of (e) coating the tablets formed in step (d).

In an embodiment, the excipients of step (a) comprise mannitol, microcrystalline cellulose, polyvinylpolypyrrolidone, and polyvinylpyrrolidone. In another embodiment, the excipients of step (a) further comprise sodium dodecyl sulfate.

In an embodiment, the suitable excipients of step (b) comprise microcrystalline cellulose, colloidal silicon dioxide, and polyvinylpolypyrrolidone.

In another aspect, provided herein is a process for the production of a tablet comprising 2-fluoro-N-methyl-4-[7-(quinolin-6-ylmethyl)imidazo[1,2-b][1,2,4]triazin-2-yl]benzamide or a pharmaceutically acceptable salt thereof, wherein the process comprises:
- (a) blending excipients together with 2-fluoro-N-methyl-4-[7-(quinolin-6-ylmethyl)imidazo[1,2-b][1,2,4]triazin-2-yl]benzamide or a pharmaceutically acceptable salt thereof;
- (b) granulating the mixture formed in step (a) together with water;
- (c) drying the granulate formed in step (b);
- (d) passing the granulate of step (c) through a sieve to form the intra-granular phase;
- (e) separately sieving suitable excipients as an extragranular phase;
- (f) blending together the intragranular phase formed in step (d) with the extra-granular phase formed in step (e);
- (g) adding a lubricant to the formulation to the mixture formed in step (f) and blending; and
- (h) compressing the mixture formed in step (g) into tablets.

In an embodiment, the process further comprises the step of (i) coating the tablets formed in step (h).

In an embodiment, the excipients of step (a) comprise mannitol, microcrystalline cellulose, polyvinylpolypyrrolidone, and polyvinylpyrrolidone. In another embodiment, the excipients of step (a) further comprise sodium dodecyl sulfate.

In an embodiment, the suitable excipients of step (e) comprise microcrystalline cellulose, colloidal silicon dioxide, and polyvinylpolypyrrolidone.

In another embodiment, the lubricant of step (g) comprises magnesium stearate.

EXAMPLES

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. Examples of Tablet Formulations Comprising Compound I

TABLE 1a

Example of a Tablet Formulation

| Ingredient | Excipient Function | % | 50 mg mg/dose | 100 mg mg/dose | 200 mg mg/dose |
|---|---|---|---|---|---|
| Compound I•2HCl[1] | — | 23.54 | 58.850 | 117.700 | 235.4 |
| mannitol (e.g., Mannitol PH) | diluent/filler | 20.00 | 50.000 | 100.000 | 200.00 |
| microcrystalline cellulose (e.g., Avicel PH101 or cellulose MKGR) | diluent/filler | 41.01 | 102.525 | 205.05 | 410.1 |
| Sodium dodecyl sulfate (e.g., Duponol C) | surfactant | 0.20 | 0.500 | 1.000 | 2.00 |
| crospovidone (e.g., Polyvinylpolypyrrolidone XL) | disintegrant | 10.00 | 25.00 | 50.00 | 100.00 |
| polyvinylpyrrolidone (e.g., Polyvinylpyrrolidone K30 PH) | disintegrant | 4.00 | 10.000 | 20.000 | 40.00 |
| colloidal silicon disoxide (e.g., Aerosil 200) | glidant | 0.50 | 1.250 | 2.500 | 5.00 |
| Magnesium stearate | lubricant | 0.75 | 1.875 | 3.750 | 7.50 |
| Total (tablet) | | 100.00 | 250.000 | 500.000 | 1000.00 |

[1]50 mg of Compound I corresponds to 58.85 mg of Compound I dihydrochloric acid salt and 100 mg of Compound I corresponds to 117.70 mg of Compound I dihydrochloric acid salt. The salt factor, or the multiplier to determine the amount of the dihydrochloric acid salt to achieve a desired amount of Compound I free base, is 1.177.

TABLE 1b

Example of a tablet formulation comprising an intragranular and extragranular phase

| Ingredient | Excipient Function | % | 50 mg mg/dose | 100 mg mg/dose | 200 mg mg/dose |
|---|---|---|---|---|---|
| INTRA-GRANULAR | | | | | |
| Compound I•2HCl[1] | — | 23.54 | 58.850 | 117.700 | 235.4 |
| Mannitol PH | diluent/filler | 20.00 | 50.000 | 100.000 | 200.00 |
| Avicel PH101 | diluent/filler | 20.26 | 50.650 | 101.300 | 202.6 |

TABLE 1b-continued

Example of a tablet formulation comprising an intragranular and extragranular phase

| Ingredient | Excipient Function | % | 50 mg mg/dose | 100 mg mg/dose | 200 mg mg/dose |
|---|---|---|---|---|---|
| Duponol C | surfactant | 0.20 | 0.500 | 1.000 | 2.00 |
| Polyvinylpolypyrrolidone XL | disintegrant | 5.00 | 12.500 | 25.000 | 50.00 |
| Polyvinylpyrrolidone K30 PH | disintegrant | 4.00 | 10.000 | 20.000 | 40.00 |
| Subtotal (Intra-granular phase) | | 73.00 | 182.500 | 365.000 | 730.00 |
| EXTRA-GRANULAR | | | | | |
| Cellulose MKGR | diluent/filler | 20.75 | 51.875 | 103.750 | 207.5 |
| Aerosil 200 | glidant | 0.50 | 1.250 | 2.500 | 5.00 |
| Polyvinylpolypyrrolidone XL | disintegrant | 5.00 | 12.500 | 25.000 | 50.00 |
| Magnesium stearate | lubricant | 0.75 | 1.875 | 3.750 | 7.50 |
| Total (tablet) | | 100.00 | 250.000 | 500.000 | 1000.00 |
| OPTIONAL FILM-COATING | | | | | |
| Basis Black | | | 0.000 | 0.123 | 1.30 |
| Basis Red | | | 0.020 | 1.131 | 4.68 |
| Basis Yellow | | | 0.800 | 0.000 | 15.34 |
| Basis White | | | 9.180 | 14.746 | 4.68 |
| Total (film-coated tablet) | | | 260.000 | 516.000 | 1026.00 |

[1] 50 mg of Compound I corresponds to 58.85 mg of Compound I dihydrochloric acid salt and 100 mg of Compound I corresponds to 117.70 mg of Compound I dihydrochloric acid salt. The salt factor, or the multiplier to determine the amount of the dihydrochloric acid salt to achieve a desired amount of Compound I free base, is 1.177.

TABLE 1c

Examples of tablet formulations with varying amounts of disintegrants

| Ingredient | Excipient Function | % weight of the tablet | | | |
|---|---|---|---|---|---|
| INTRA-GRANULAR | | | | | |
| Compound I•2HCl | — | 24.54 | 24.54 | 24.54 | 24.54 |
| Mannitol PH | diluent/filler | 20.00 | 20.00 | 20.00 | 21.00 |
| Avicel PH101 | diluent/filler | 19.26 | 19.26 | 19.26 | 19.26 |
| Duponol C | surfactant | 0.20 | 0.20 | 0.20 | 0.20 |
| Polyvinylpolypyrrolidone XL | disintegrant | 5.00 | 5.00 | 5.00 | 4.00 |
| Polyvinylpyrrolidone K30 | disintegrant | 4.00 | 4.00 | 4.00 | 4.00 |
| Subtotal (Intra-granular phase) | | 73.00 | 73.00 | 73.00 | 73.00 |
| EXTRA-GRANULAR | | | | | |
| Cellulose MKGR | diluent/filler | 20.75 | 22.75 | 24.75 | 23.75 |
| Aerosil 200 | glidant | 0.50 | 0.50 | 1.50 | 2.50 |
| Polyvinylpolypyrrolidone XL | disintegrant | 5.00 | 3.00 | 0.00 | 0.00 |
| Magnesium stearate | lubricant | 0.75 | 0.75 | 0.75 | 0.75 |
| Total (tablet) | | 100.00 | 100.00 | 100.00 | 100.00 |
| OPTIONAL FILM-COATING | | | | | |

TABLE 1d

Examples of tablet formulations with different ratios
of the intragranular phase to extragranular phase

| Ingredient | Excipient Function | % weight of the tablet | | |
|---|---|---|---|---|
| INTRA-GRANULAR | | | | |
| Compound I•2HCl | — | 24.54 | 24.54 | 24.54 |
| Mannitol PH | diluent/filler | 25.00 | 28.00 | 15.00 |
| Avicel PH101 | diluent/filler | 24.26 | 26.26 | 14.26 |
| Duponol C | surfactant | 0.20 | 0.20 | 0.20 |
| Polyvinylpolypyrrolidone XL | disintegrant | 5.00 | 8.00 | 5.00 |
| Polyvinylpyrrolidone K30 | disintegrant | 4.00 | 4.00 | 4.00 |
| Subtotal (Intra-granular phase) | | 83.00 | 91.00 | 63.00 |
| EXTRA-GRANULAR | | | | |
| Cellulose MKGR | diluent/filler | 10.75 | 5.75 | 23.75 |
| Aerosil 200 | glidant | 0.50 | 0.50 | 2.50 |
| Polyvinylpolypyrrolidone XL | disintegrant | 5.00 | 2.00 | 5.00 |
| Magnesium stearate | lubricant | 0.75 | 0.75 | 0.75 |
| Mannitol | | — | — | 5.0 |
| Total (tablet) | | 100.00 | 100.00 | 100.00 |
| OPTIONAL FILM-COATING | | | | |

Notes on the Formulation:

2-fluoro-N-methyl-4-[7-(quinolin-6-ylmethyl)imidazo[1,2-b][1,2,4]triazin-2-yl]benzamide dihydrochloride is a highly soluble compound at low pH (7.2 mg/mL at pH 1), but displays low solubility at pH 6.8 and above (0.0793 mg/mL at pH 6.8). Addition of surfactants or other polymeric excipients capable of delaying drug precipitation at higher pHs may contribute to increased in vivo exposure.

2-fluoro-N-methyl-4-[7-(quinolin-6-ylmethyl)imidazo[1,2-b][1,2,4]triazin-2-yl]benzamide dihydrochloride has a gelling behavior, mostly prominent at pHs above 3.5, which can compromise tablet disintegration and dissolution rate. Drug load and disintegrant type/levels can influence this behavior and need to be carefully selected to ensure adequate in vitro performance.

Example 2. Example of a Manufacturing Process for Tablets Comprising Compound I

The process described below may be reasonably adjusted, while maintaining the same basic production steps, to compensate for different batch sizes and/or equipment characteristics, and/or on the basis of experience.

1. Sieve Mannitol and blend it together with 2-fluoro-N-methyl-4-[7-(quinolin-6-ylmethyl)imidazo[1,2-b][1,2,4]triazin-2-yl]benzamide dihydrochloride, Duponol, crospovidone, Polyvinylpyrrolidone K30 and Avicel PH 101.
2. Granulate the blend from bullet point 1 with water and dry the granulate.
3. Pass the granulate from bullet point 2 through a sieve.
4. Sieve the external phase consisting of microcrystalline cellulose (Cellulose MK GR), crospovidone (polyvinylpolypyrrolidone), and Aerosil 200.
5. Blend together the mixtures from bullet points 3 and 4.
6. Pass Magnesium Stearate through a sieve and add to the formulation from bullet point 5 and blend.
7. Compress the blend from bullet point 6 into tablets.
8. Optionally coat the tablets to form film-coated tablets.
An illustration of this process is found in FIG. 1.

Notes on the Manufacturing Process:

2-fluoro-N-methyl-4-[7-(quinolin-6-ylmethyl)imidazo[1,2-b][1,2,4]triazin-2-yl]benzamide dihydrochloride has a very low bulk density (0.085 g/mL), which justifies the need of a densification step prior tabletting. Wet granulation was identified as the most suitable technology for this compound. As opposed to roller compaction, formulations processed with wet granulation technology showed adequate balance among tablet friability, disintegration and dissolution rate.

Excipient levels, specifically those of surfactants like sodium dodecyl sulfate, should be kept to a minimum to comply with recommended permitted daily exposure values.

Example 3: Dog Pharmacokinetic Studies

Data from a dog PK study comparing the 2-fluoro-N-methyl-4-[7-(quinolin-6-ylmethyl)imidazo[1,2-b][1,2,4]triazin-2-yl]benzamide dihydrochloride hard gelatin capsule (HGC) presently used in clinics against two prototype tablet formulations was also used as guidance for formulation/process development of the tablet clinical service form. Those studies were performed with a 50 mg dosage strength and show that the tablet formulation manufactured by wet granulation using SDS as surfactant results in similar 2-fluoro-N-methyl-4-[7-(quinolin-6-ylmethyl)imidazo[1,2-b][1,2,4]triazin-2-yl]benzamide dihydrochloride plasma levels as the 2-fluoro-N-methyl-4-[7-(quinolin-6-ylmethyl)imidazo[1,2-b][1,2,4]triazin-2-yl]benzamide dihydrochloride HGC.

We claim:

1. A tablet comprising 2-fluoro-N-methyl-4-[7-(quinolin-6-ylmethyl)imidazo[1,2-b][1,2,4]triazin-2-yl]benzamide dihydrochloric acid salt, wherein the tablet further comprises:
   (a) an intra-granular phase; and
   (b) an extra-granular phase,
   wherein the tablet comprises, by weight of the tablet, 10-30% 2-fluoro-N-methyl-4-[7-(quinolin-6-ylmethyl)imidazo[1,2-b][1,2,4]triazin-2-yl]benzamide dihydrochloric acid salt, 50-70% of one or more fillers, 3-20% of one or more disintegrants, 0.2-2% of one or more lubricants, and 0.2-2% of one or more glidants.

2. The tablet of claim 1, wherein the intra-granular phase comprises 2-fluoro-N-methyl-4-[7-(quinolin-6-ylmethyl)imidazo[1,2-b][1,2,4]triazin-2-yl]benzamide dihydrochloric acid salt, mannitol, microcrystalline cellulose, polyvinylpolypyrrolidone, and polyvinylpyrrolidone.

3. The tablet of claim 1, wherein the intra-granular phase comprises, by weight of the tablet, 10-30% 2-fluoro-N-methyl-4-[7-(quinolin-6-ylmethyl)imidazo[1,2-b][1,2,4]triazin-2-yl]benzamide dihydrochloric acid salt; 10-30% mannitol; 10-30% microcrystalline cellulose; and 0.1-10.0% each of polyvinylpolypyrrolidone, and polyvinylpyrrolidone.

4. The tablet of claim 1, wherein the intra-granular phase comprises, by weight of the tablet, about 24% 2-fluoro-N-methyl-4-[7-(quinolin-6-ylmethyl)imidazo[1,2-b][1,2,4]triazin-2-yl]benzamide dihydrochloric acid salt; about 20% mannitol; about 20% microcrystalline cellulose; about 5% polyvinylpolypyrrolidone; and about 4% polyvinylpyrrolidone.

5. The tablet of claim 1, wherein the extra-granular phase comprises microcrystalline cellulose, colloidal silicon dioxide, polyvinylpolypyrrolidone, and magnesium stearate.

6. The tablet of claim 1, wherein the extra-granular phase comprises, by weight of the tablet, 10-30% microcrystalline cellulose and 0.1-10.0% each of colloidal silicon dioxide, polyvinylpolypyrrolidone, and magnesium stearate.

7. The tablet of claim 1, wherein the extra-granular phase comprises, by weight of the tablet, about 21% microcrystalline cellulose; about 0.5% colloidal silicon dioxide; 5% polyvinylpolypyrrolidone; and about 0.75% magnesium stearate.

8. The tablet of claim 1, comprising an amount of 2-fluoro-N-methyl-4-[7-(quinolin-6-ylmethyl)imidazo[1,2-b][1,2,4]triazin-2-yl]benzamide dihydrochloric acid salt, wherein the amount corresponds to 5 mg, 10 mg, 20 mg, 25 mg, 40 mg, 50 mg, 75 mg, 100 mg, 125 mg, 150 mg, 200 mg, 250 mg, or 500 mg of the free base form.

9. A tablet comprising 2-fluoro-N-methyl-4-[7-(quinolin-6-ylmethyl)imidazo[1,2-b][1,2,4]triazin-2-yl]benzamide, or a pharmaceutically acceptable salt thereof, wherein the tablet comprises:

(a) an intragranular phase comprising, by weight:
  10-30% of 2-fluoro-N-methyl-4-[7-(quinolin-6-ylmethyl) imidazo[1,2-b][1,2,4]triazin-2-yl]benzamide dihydrochloric acid salt,
  10-30% of mannitol,
  10-30% of microcrystalline cellulose,
  0-1% of sodium dodecyl sulfate,
  1-10% of polyvinylpolypyrrolidone, and
  1-10% of polyvinylpyrrolidone; and
(b) an extragranular phase comprising, by weight:
  10-30% of microcrystalline cellulose,
  0.1-1% of colloidal silicon dioxide,
  1-10% of polyvinylpolypyrrolidone, and
  0.1-1% of magnesium stearate;
wherein the percentages given for the respective ingredients are relative to the total weight of the tablet.

* * * * *